United States Patent [19]
Nielsen et al.

[11] Patent Number: 5,837,513
[45] Date of Patent: Nov. 17, 1998

[54] METHOD FOR CRYSTALLIZATION OF ENZYMES

[76] Inventors: Niels-Viktor Nielsen, Ryegade 5, DK-4060 Kirke Saaby, Denmark; Torben Kjærsgaard Nielsen, Tinggårdsvænget 90, Tune, DK-4000 Roskilde, Denmark

[21] Appl. No.: 472,357

[22] Filed: Jun. 7, 1995

Related U.S. Application Data

[63] Continuation of Ser. No. 265,984, Jun. 27, 1994, abandoned, which is a continuation of Ser. No. 865,897, which is a continuation of PCT/DK90/00341, Dec. 21, 1990.

[30] Foreign Application Priority Data

| Apr. 5, 1990 | [DK] | Denmark | 0847/90 |
| Apr. 5, 1990 | [DK] | Denmark | 0848/90 |
| Dec. 21, 1990 | [DK] | Denmark | 6540/89 |

[51] Int. Cl.⁶ ................................................. C12N 9/00
[52] U.S. Cl. ........................ 435/183; 435/221; 435/814; 435/816
[58] Field of Search ................... 435/183, 221, 435/814, 816

[56] References Cited

U.S. PATENT DOCUMENTS

| 3,623,957 | 11/1971 | Feldman | 435/222 |
| 5,041,377 | 8/1991 | Decker et al. | 435/222 |

FOREIGN PATENT DOCUMENTS

WO 89/08703  9/1989  WIPO.

OTHER PUBLICATIONS

Scopes, R.K *Protein Purification; Pinciples and Practice*, Second Edition, New York, Springer–Verlag, 1987, pp. 41–54.
Deutscher, M.P *Guide to Protein Purification* [Methods in Enzymology vol. 182], Academic Press, 1990, pp. 285–300.
McPherson, Preparation and Analysis of Protein Crystals (1989).
Steinrauf, Acta Crystallographica, vol. 12, pp. 77–79 (1959).
Melis, et al., The Journal of Biological Chemistry, vol. 258, No. 10, pp. 6255–6257 (1983).
Swan, Journal of Molecular Biology, vol. 60, No. 2, pp. 405–407 (1971).
Sheriff, et al., Journal of Molecular Biology, vol. 145, No. 2, pp. 441–451 (1981).

*Primary Examiner*—Leon B. Lankford, Jr.
*Attorney, Agent, or Firm*—Steve T. Zelson, Esq.; Valeta Gregg, Esq.

[57] ABSTRACT

A method for rapidly and inexpensively crystallizing enzymes from an impure mixture is disclosed. The yield of the enzyme is greater than 35% within twelve hours. The crystallizing agent is a salt added in a concentration which is less than the concentration necessary to crystallize the enzyme in amorphous form.

18 Claims, 2 Drawing Sheets

METHOD FOR CRYSTALLIZATION OF ENZYMES

This application is a continuation of application Ser. No. 08/265,984, filed Jun. 27, 1994, now abandoned which is a continuation application of co-pending application Ser. No. 07/856,897, filed May 14, 1992 which is a continuation of PCT/DK90/00341 filed Dec. 21, 1990, the contents of which are incorporated herein by reference.

The invention encompasses a method for crystallization of enzymes.

Enzymes are usually provided as liquids or solid materials for industrial purposes. When not provided as liquids, they are usually provided as amorphous materials, because the known methods for crystallization of enzymes usually are regarded as too expensive to be used in an industrial scale.

Thus, the purpose of the invention is the provision of a method for crystallization of enzymes, which is simple and cheap, and which is compatible to industrial requirements.

The method according to the invention is characterized by the fact that an aqueous enzyme containing liquid with an enzyme purity above 20% (i.e. the pure enzyme amounts to more than 20% of the total dry matter in the enzyme containing liquid) and with a concentration of pure enzyme protein of at least 5 g/l of enzyme containing liquid is used as a starting material, and that a crystallization agent, which is Na, K, Ca, or Mg formate, acetate or nitrate is added to the starting material to a final concentration which is smaller than the concentration needed to precipitate the enzymes in an amorphous form.

When carried out on an industrial scale, the crystals are separated in a filter, and the crystals are subsequently flushed for purification purposes. Reference is made to FIG. 1.

All crystallization agents used in the method according to the invention are easily soluble salts, i.e. salts, which in pure water at 25° C. exhibit a solubility above 5 g/l.

The above indicated starting materials are known in the art, and they can be provided for instance as described in chapter 9 ("Production of Microbial Enzymes") in Microbial Technology, 2nd edition, Vol. 1, Academic Press, Inc., 1979; and thus, an outline of recovery and purification methods for technical grade enzymes can be found in this chapter. Furthermore U.S. Pat. No. 3,795,583 describes purification methods for enzyme containing culture broths.

Surprisingly it has been found that the method according to the invention which is simple and cheap, can be carried out with a yield of up to 95%, and that it can easily be adopted to industrial practice.

Thus, the starting material for the method according to the invention for crystallization of enzymes is an aqueous enzyme containing liquid with an enzyme purity of above 20% (i.e. the pure enzyme amounts to more than 20% of the total dry matter in the enzyme containing liquid), and with a concentration of enzyme protein of at least 5 g/l of enzyme containing liquid. The time necessary for crystallization is usually between 5 and 12 hours. By addition of crystal seeds in an amount of e.g. 1% the crystallization velocity can be accelerated. The crystals are preferably separated from the supernatant by filtration.

The method according to the present invention is further described in the drawings.

Figure 1:
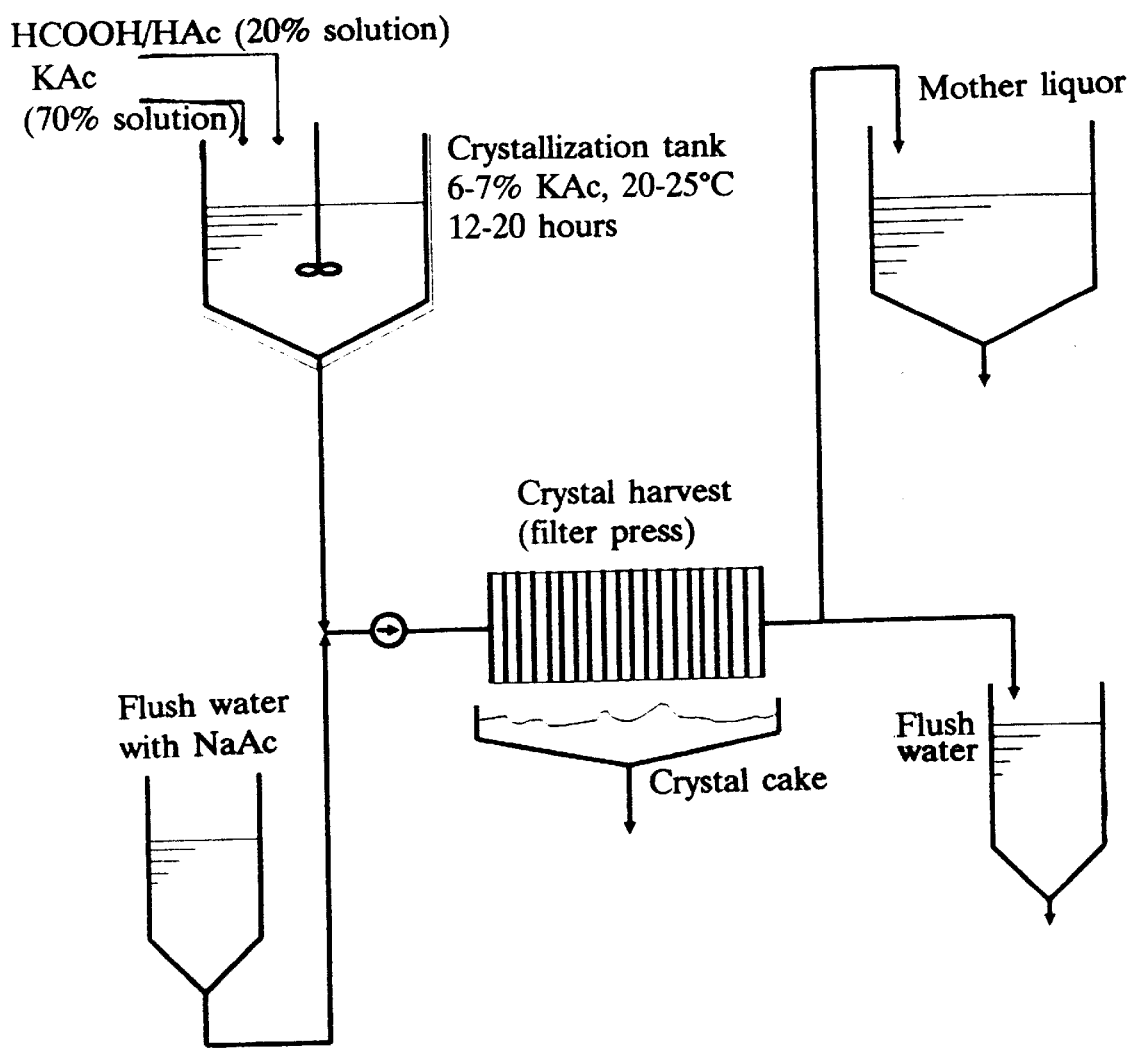
FIG. 1 is a schematic diagram of the method according to the present invention on an industrial scale.

In a preferred embodiment of the method according to the invention the crystallization agent is added to the starting material to a final concentration corresponding to an added amount of crystallization agent of from 0.02 to 1.7M of crystallization agent, preferably from 0.05 to 1.6M, more preferably from 0.10 to 1.5M.

In a preferred embodiment of the method according to the invention the enzyme is a protease, lipase, amylase, cellulase, hemicellulase, pectinase, amidase or oxidase. These enzymes are commonly used as additives in detergents, and thus, when crystalline enzymes are desirable in the detergent industry, this embodiment is preferred. Also protein engineered variants of these enzymes are within the scope of the invention.

In a preferred embodiment of the method according to the invention the enzyme is a protease and the protease is a Subtilisin type protease, preferably SAVINASE® or a protein engineered variant thereof. Other examples of such proteases are ALCALASE®, Subtilisin NOVO or protein engineered variants of these, which are very commonly used as additives in detergents, and thus, when crystalline SAVINASE®, ESPERASE®, ALCALASE®, Subtilisin NOVO or protein engineered variants of these is desirable in the detergent industry, this embodiment is preferred.

DK patent application No. 872/86 describes a method for crystallization of an enzyme containing solution, wherein a supersaturated solution is crystallized at a pH close to the isoelectric point of the enzyme.

U.S. Pat. No. 4,699,882 describes a crystallization method specifically directed to glucose isomerase. The crystallization agents used are magnesium sulphate and ammonium sulphate. However, the crystallization agents used according to the invention exhibit technical advantages in comparison to these known crystallization agents. Thus, the crystallization agents according to the invention are better for control of the crystallization process, and also, they exhibit a lesser tendency to precipitate colored impurities.

WO 89/08703 describes a Subtilisin crystallization process, which as an imperative step uses a crystallization agent, which is a halide salt, and which can only be performed satisfactorily below around 10° C.

Thus, all these prior art methods differ substantially from the method according to the invention.

EXAMPLES 1-4

The starting material for the crystallization of Savinase® crystals is prepared in the following manner.

To 1 kg of Savinase® fermentation broth (U.S. Pat. No. 3,723,250) are added 7.5 g of $CaCl_2.2H_2O$ and 1 liter of water. The pH is adjusted to 8.0 with an aqueous sodium hydroxide solution. The suspension is then flocculated by addition of Superfloc C 521 flocculation agent (approx. 15 g/liter of broth) and Superfloc A 130 flocculation agent (approx. 0.2 g/liter of broth). The flocculated suspension is centrifuged and the supernatant is filtered on an appropriate filter sheet in order to obtain a clear liquid. The filtrate is concentrated by evaporation to a value of RI (refractive index) of 12% and then heated to approx. 38° C. At this temperature sodium sulphate (250 g/kg enzyme solution) is added stepwise to the solution with rapid mixing.

The precipitate is filtered off and is reslurried in cold (<5° C.) water (3–5 liters of water/kg of filter cake). The undissolved material is removed by filtration and the clear filtrate is ultra- and diafiltered to a point where the value of the RI (Refractometer Index) dry matter in the permeate is less than 0.5% and the value of the RI dry matter in the concentrate is between 10–16%. The proteolytic activity is 18–22 KNPU/g (Kilo Novo Protease Units/gram).

The resulting concentrate exhibits a content of pure Savinase® protease on a dry matter basis above 25% w/w.

To the starting material, i.e. the above indicated concentrate, is added 7% of calcium formate (0.54M added) serving as a precipitation agent, at 20°–25° C. and a pH value of approximately 5.0. The mixture is seeded with Savinase® crystals (approx. 1% w/w) and then gently agitated, and after 3–6 hours a powerful precipitate of crystalline Savinase® can be observed. The amount of the crystal sludge is approx. 20% of the total volume and exhibits an enzyme activity of approx. 86 KNPU/g. The precipitation yield on the basis of KNPU is around 81%.

The following Examples 2–4 were carried out with the same Savinase® concentrate, seeding procedure, temperature (20°–24° C.) and pH (5.0). All the generated crystal sludges had an activity of about 80 KNPU/g.

The variable parameters in Examples 2–4 appear from the following table.

TABLE 1

| Example no. | Precipitation agent | Concentration of added precipitation agent | % sludge | % Yield |
|---|---|---|---|---|
| 2 | Ca(CHOO)$_2$ | 0.38 M | 17.5 | 73 |
| 3 | K(CH$_3$COO) | 0.82 M | 15.0 | 74 |
| 4 | K(CH$_3$COO) | 1.00 M | 16.0 | 78 |

EXAMPLES 5–69

It has been found that the crystallization process is dependent on the following parameters:

pH: with increasing pH the crystal size decreases, and the crystallization velocity increases.
Salt concentration: with increasing salt concentration the crystallization yield increases, the crystallization velocity increases, and the crystal size decreases.
Salt type: the crystallization performance varies from salt to salt.
Temperature: with increasing temperature the crystallization velocity increases, and the crystal size decreases.
Enzyme concentration: with increasing enzyme concentration the crystallization velocity increases, the crystallization yield increases, and the crystal size decreases.
Enzyme purity: with increasing enzyme purity the crystallization velocity increases, and the crystallization yield increases.

The following examples 5–18, which illustrate the above indicated pH dependency and the salt concentration dependency, were carried out with a Savinase® concentrate, made by the method mentioned in Examples 1–4. The temperature was kept at 20°–25° C. and the concentration of enzyme was approx. 55 g/l. The crystallization agent was potassium acetate. The enzyme purity was approximately 35%.

| Example no. | pH | Mol potassium acetate added/l | crystallization start, comment |
|---|---|---|---|
| 5 | 4.0 | 0.8 | no crystallization |
| 6 | 4.5 | 0.8 | 1–2 h, 20–50 μm crystals |
| 7 | 5.5 | 0.8 | ½–1 h, 10–50 μm crystals |
| 8 | 6.5 | 0.8 | ≈½ h, 5–50 μm crystals |
| 9 | 7.5 | 0.8 | ≈½ h, 5–10 μm crystals |

| Example no. | pH | Mol potassium acetate added/l | crystallization yield, comment |
|---|---|---|---|
| 10 | 5.5 | 0.05 | no crystallization |
| 11 | 5.5 | 0.10 | no crystallization |
| 12 | 5.5 | 0.20 | no crystallization |
| 13 | 5.5 | 0.40 | ≈75%, 10–30 μm crystals |
| 14 | 5.5 | 0.60 | ≈84%, 5–20 μm crystals |
| 15 | 5.5 | 0.80 | ≈84%, 1–20 μm crystals |
| 16 | 5.5 | 1.20 | ≈84%, 1–20 μm crystals |
| 17 | 5.5 | 1.40 | ≈87%, 1–10 μm crystals |
| 18 | 5.5 | >1.60 | amorphous fragments |

Figure 2:
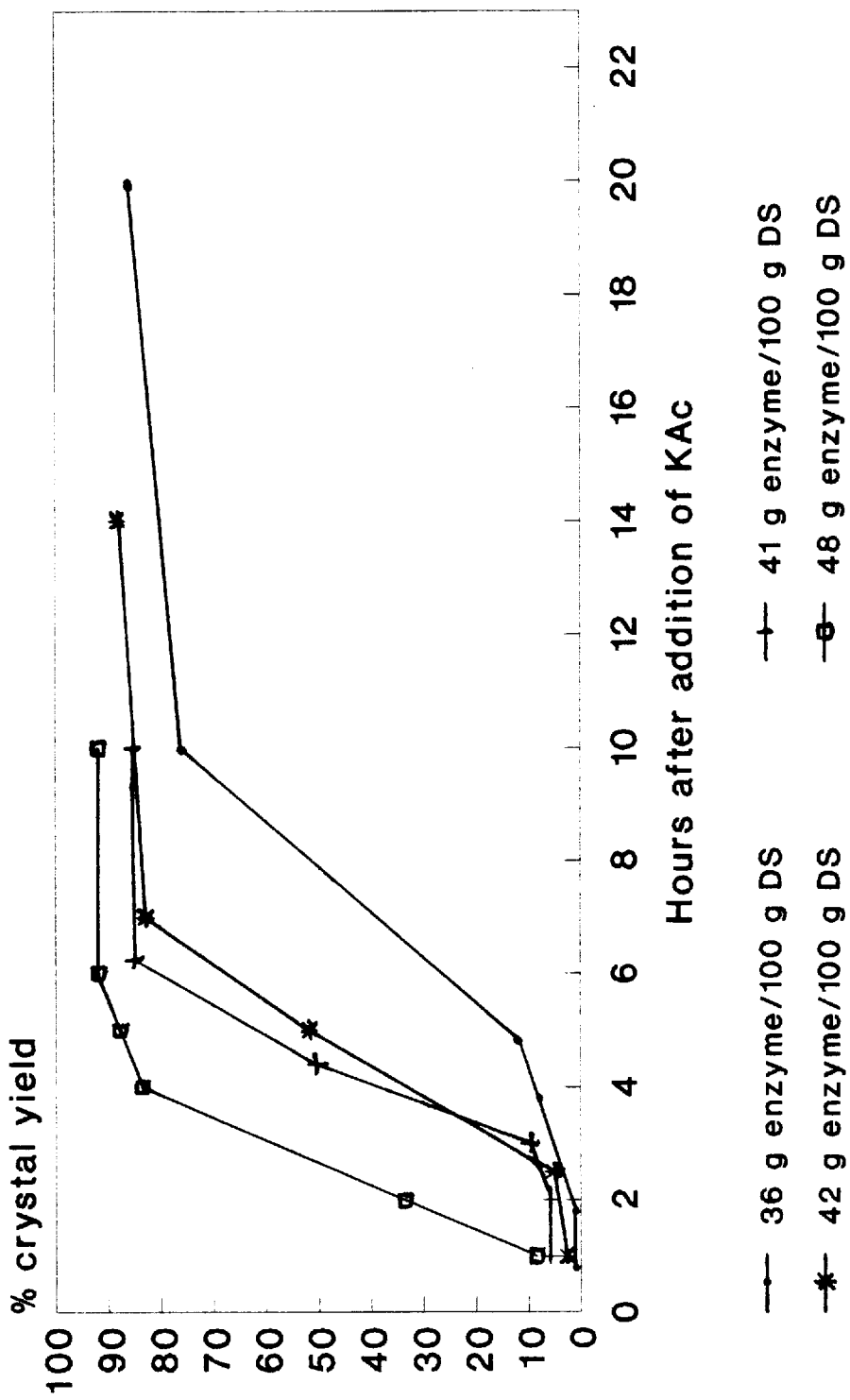
FIG. 2 is a graph depicting the % crystallization of SAVINASE® as a function of enzyme purity.

Reference is made to FIG. 2, which shows crystallization performance (Savinase®) as a function of enzyme purity. FIG. 2 shows that the crystallization velocity and the crystallization yield increases with increasing enzyme purity.

The following examples 19–25 which show the crystallization performance as a function of enzyme concentration, were carried out at 20°–25° C., with 0.8 mol added potassium acetate/l and at pH 4.9. The enzyme purity is about 38% (DS (dry substance) basis). The Savinase® samples are taken from different stages in the final ultrafiltration in the recovery process mentioned in Examples 1–4, corresponding values in the column "g enzyme/l".

| Example no. | g enzyme/l | Start of crystallization | Yield |
|---|---|---|---|
| 19 | 8.6 | ÷ | 0% |
| 20 | 17.0 | 2–3 h | 70% |
| 21 | 25.0 | 1 ½–2 h | 85% |
| 22 | 33.0 | 1 ½ h | 88% |
| 23 | 41.0 | ½–1 h | 90% |
| 24 | 50.0 | ½–1 h | 92% |
| 25 | 58.0 | ½–1 h | 94% |

The following examples 26–29 which show the crystallization performance as a function of enzyme temperature, are carried out with 0.51 mol added potassium acetate/l, pH 5.5 and an enzyme concentration at about 55 g/l. The enzyme purity is about 36% (DS basis). Maximum crystallization time: 12 hours.

| Example no. | Temperature | Start of crystallization | Yield |
|---|---|---|---|
| 26 | 10° C. | >10 hours | <1% |
| 27 | 15° C. | 3 hours | 78% |
| 28 | 20° C. | 2 hours | 85% |
| 29 | 30° C. | ¾ hours | 93% |

The following examples 30–69 show that the crystallization process can easily be used with other subtilisins such as Alcalase® and Durazym®.

The starting material for the crystallization is prepared by a recovery process which is very similar to that indicated in Examples 1–4.

In the case of Alcalase®, during the flocculation step besides CaCl$_2$ about 4 g of NaAlO$_2$ per l of fermentation broth is added. The product will end up with a proteolytic activity at about 3.5 AU/g.

Durazym®, which is a protein engineered version of Savinase®, is prepared analogously to the crystallization of Savinase® in Examples 1–4. The product will end up with a proteolytic activity at about 19 DPU/g.

Before crystallization both enzymes have an enzyme purity above 25% measured on dry matter basis.

In the following examples 30–34 the enzyme is Alcalase®, and the pH during the crystallization is 4.5–8.5, the temperature is between 20° and 25° C., the crystallization agent is sodium formate, which is added in a concentration of 1.5 M/l, the enzyme concentration is approximately 66 g/l, and the enzyme purity is 50%.

| Example no | pH | Start of crystallization | Yield |
| --- | --- | --- | --- |
| 30 | 4.5 | 1 hour | 92% |
| 31 | 5.5 | 1 hour | 93% |
| 32 | 6.5 | ½ hour | 95% |
| 33 | 7.5 | ½ hour | ≈93% |
| 34 | 8.5 | <<½ hour | ≈93% |

In the following examples in which Alcalase® and different crystallization agents are used the pH during the crystallization is between 4.5 and 5.0, the temperature is between 20° and 25° C., the crystallization time is between 6 and 24 hours, the enzyme concentration is approx. 66 g/l and the enzyme purity is 50%.

Enzyme: Alcalase*

| Example no. | Salt | M salt added/l | Yield |
| --- | --- | --- | --- |
| 35 | Na(CH$_3$COO) | 0.7 | 35% |
| 36 | Na(CH$_3$COO) | 1.2 | 70% |
| 37 | Na(CH$_3$COO) | 1.7 | 78% |
| 38 | Na(CHOO) | 0.9 | 80% |
| 39 | Na(CHOO) | 1.1 | 90% |
| 40 | Na(CHOO) | 1.4 | 96% |
| 41 | Ca(CHOO)$_2$ | 0.4 | 45% |
| 42 | Ca(CHOO)$_2$ | 0.8 | 60% |
| 43 | Ca(CHOO)$_2$ | 0.9 | 78% |

In the following examples which are performed with Alcalase® and with crystallization with sodium formate at different enzyme concentrations the pH during the crystallization is between 4.5 and 5.0, the temperature is between 20° and 25° C., the crystallization time is 12 hours (at 20° to 25° C.) plus 12 hours at 10° C. The enzyme concentration is approx. 66 g/l, the enzyme purity is 50%, and the salt is added in a dosage of 1.5 Mol/l.

| Example no. | g enzyme/l | Start of crystallization | Yield |
| --- | --- | --- | --- |
| 44 | 19 | 2 hours | 60% |
| 45 | 29 | 1 hour | 81% |
| 46 | 40 | 1 hour | 86% |
| 47 | 50 | ¾ hour | 90% |
| 48 | 58 | <¾ hour | 93% |

The following examples with Alcalase® which illustrate crystallization performance as a function of temperatures are carried out at pH 4.5 and a temperature between 5° and 30° C. The sodium formate is added in an amount of 1.5 Mol/l. The enzyme concentration is approx. 66 g/l and the enzyme purity is 50%. The crystallization time is 12 hours at the temperature specified plus 12 hours at 10° C.

| Example no. | Temperature | Start of crystallization | Yield |
| --- | --- | --- | --- |
| 49 | 5° C. | >12 hours | — |
| 50 | 15° C. | >12 hours | — |
| 51 | 20° C. | 1 hour | 90% |
| 52 | 25° C. | <½ hour | ≈88% |
| 53 | 30° C. | <½ hour | ≈86% |

The following examples which illustrate crystallization performance of Alcalase® as a function of enzyme temperature are carried out at pH 5.0 and at a temperature between 15° and 30° C. The dosage of calcium formate is 0.8 Mol added/l. The enzyme concentration is approx. 63 g/l and the purity is 50%.

The crystallization time is 12 hours (at the specified temperature) plus 12 hours at 10° C.

| Example no. | Temperature | Start of crystallization | Yield/ crystal size |
| --- | --- | --- | --- |
| 54 | 15° C. | 10 hours | 4%/50–80 μm |
| 55 | 20° C. | 4 hours | 16%/40–80 μm |
| 56 | 25° C. | 2 ¼ hour | 46%/10–60 μm |
| 57 | 30° C. | <½ hour | 49%/15–40 μm |

The following examples which illustrate crystallization of Alcalase® at different pH values the pH is varied from 4.5 to 8.5, the temperature is between 20° and 25° C., the salt dosage is 0.8 Mol added/l the enzyme concentration is approx. 66 g/l and the enzyme purity is 50%. Salt: potassium acetate.

| Example no. | pH | Start of crystallization | Yield/ crystal size |
| --- | --- | --- | --- |
| 58 | 4.5 | 3 ½ hour | 55%/30–70 μm |
| 59 | 5.5 | 1 ½ hour | ≈60%*)/1–10 μm |
| 60 | 6.5 | 1 ½ hour | ≈60%*)/1–10 μm |
| 61 | 7.5 | 1 hour | ≈60%*)/1–10 μm |
| 62 | 8.5 | ¼ hour | ≈60%*)/1–10 μm |

*)The crystals are very small and therefore hard to separate from the mother liquor The following examples with Durazym®, which show crystallization with different crystallization agents are carried out at pH 4.9 and a temperature between 20° and 25° C. The enzyme concentration is approx. 48 g/l and the enzyme purity is approx. 30%.

Enzyme: Durazym*

| Example no. | Salt | M salt added/l | Yield |
| --- | --- | --- | --- |
| 63 | Na(CHOO) | 0.6 | 42% |
| 64 | Na(CHOO) | 1.1 | 90% |
| 65 | Na(CHOO) | 1.5 | 96% |
| 66 | K(CH$_3$COO) | 0.6 | 62% |
| 67 | K(CH$_3$COO) | 0.8 | 83% |
| 68 | K(CH$_3$COO) | 1.2 | 86% |

EXAMPLE 69

Crystallization of Candida lipase B

Candida lipase B is described in WO 88/02775, from which is appears that this lipase can be produced by means of *Candida antarctica* DMS 3855.

After fermentation the culture broth is pretreated by addition of 0.25 l of water per liter of culture broth. pH is adjusted to 8.0 by means of an aqueous solution of NaOH.

The suspension is filtered on a drum filter, which is precoated with Dicalite 4208 kiselguhr. The filtrate is subsequently filtered on appropriate filter plates in order to obtain a completely clear liquid. Finally an ultrafiltration and a diafiltration is carried out until a value of RI (Refrectometer Index) dry substance in the concentrate of around 12% and until the value of RI dry substance in the permeate is less than 2%. Finally a sterile filtration is carried out. This filtrate which exhibits a lipase activity of approx. 25 KLU/g and a pH of 7.0 is the starting material for the crystallization. To the starting material is added 4–6% salt, which is $CH_3COOK(KAc)$ or HCOONa. After a few minutes a powerful precipitate of crystalline Candida lipase B is formed, and 2–5 hours later the crystalline precipitate amounts to around 20% of the total volume. The crystals exhibit an activity of 65–70 KLU/g, and the yield exceeds 80%. The crystals are small and needle shaped.

We claim:

1. A rapid and inexpensive method for crystallizing an enzyme from an impure enzyme solution, comprising
   (a) obtaining an impure enzyme preparation, wherein the enzyme is present in an amount of more than 20% of the total dry matter;
   (b) adding an effective amount of a crystallization agent to the impure enzyme preparation of step(a); wherein
      (i) the crystallization agent is one or more salts selected from the group consisting of sodium formate, sodium acetate, sodium nitrate, potassium formate, potassium acetate, potassium nitrate, calcium formate, calcium acetate, calcium nitrate, magnesium formate, magnesium acetate and magnesium nitrate;
      (ii) the concentration of the crystallization agent added to the aqueous solution is less than a concentration of the crystallization agent which precipitates the enzyme in an amorphous form;
      (iii) the method obtains a yield of the crystallized enzyme of at least 35% within 12 hours, and
      (iv) wherein said method is suitable for industrial use.

2. The method according to claim 1, wherein the crystallization agent is calcium or magnesium nitrate.

3. The method according to claim 1, wherein the crystallization agent is magnesium acetate.

4. The method according to claim 1, wherein the crystallization agent is potassium acetate.

5. The method according to claim 1, wherein the concentration of the crystallization agent in the solution is from 0.02 to 1.7M.

6. The method according to claim 5, wherein the concentration of the crystallization agent in the solution is from 0.05 to 1.6M.

7. The method according to claim 6, wherein the concentration of the crystallization agent in the solution is from 0.10 to 1.5M.

8. The method according to claim 1, wherein the enzyme is a protease, lipase, amylase, cellulase, hemicellulase, pectinase, amidase or oxidase.

9. The method according to claim 8, wherein the enzyme is a protease.

10. The method according to claim 9, wherein the enzyme is a subtilisin.

11. The method according to claim 8, wherein the enzyme is a lipase.

12. The method according to claim 8, wherein the enzyme is an amylase.

13. The method according to claim 1 which is carried out at a temperature between 15° and 30° C.

14. The method according to claim 1 which is carried out at a pH between 4.5 and 7.5.

15. The method according to claim 1, wherein the amount of the enzyme present in the aqueous solution is about 20–50% of the total dry matter.

16. The method according to claim 1, wherein the time for crystallizing the enzyme is between 5 and 12 hours.

17. The method of claim 1 wherein the enzyme is present in a concentration of at least 5 g/l.

18. The method according to claim 17, wherein concentration of the enzyme in the aqueous solution is between about 5–66 g/l.

* * * * *

UNITED STATES PATENT AND TRADEMARK OFFICE
CERTIFICATE OF CORRECTION

PATENT NO. : 5,837,513
DATED : November 17, 1998
INVENTOR(S) : Nielsen et al.

It is certified that error appears in the above-identified patent and that said Letters Patent is hereby corrected as shown below:

Title Page, [30], delete "Dec. 21, 1990" and insert --Dec. 21, 1989--.

Title Page, [63], delete "865,897" and insert --856,897, May 14, 1992--;

Col. 8, Claim 18, line 37, before "concentration" insert --the--,

Signed and Sealed this

Eleventh Day of January, 2000

Attest:

Q. TODD DICKINSON

*Attesting Officer*   Acting Commissioner of Patents and Trademarks